US012588930B2

(12) United States Patent
Whittaker et al.

(10) Patent No.: US 12,588,930 B2
(45) Date of Patent: Mar. 31, 2026

(54) DEVICES, SYSTEMS, AND METHODS OF USE FOR DELIVERY OF MATERIALS IN COMBINATION WITH INTRAMEDULLARY DEVICES

(71) Applicant: Curvafix, Inc., Bellevue, WA (US)

(72) Inventors: Eric Whittaker, Edmonds, WA (US); Steven Dimmer, Bellevue, WA (US); Blake Matsuzaki, Bothell, WA (US)

(73) Assignee: Curvafix, Inc., Bellevue, WA (US)

( * ) Notice: Subject to any disclaimer, the term of this patent is extended or adjusted under 35 U.S.C. 154(b) by 380 days.

(21) Appl. No.: 18/164,584

(22) Filed: Feb. 4, 2023

(65) Prior Publication Data

US 2023/0248392 A1 Aug. 10, 2023

Related U.S. Application Data

(60) Provisional application No. 63/267,590, filed on Feb. 4, 2022.

(51) Int. Cl.
A61B 17/58 (2006.01)
A61B 17/70 (2006.01)

(52) U.S. Cl.
CPC .............. A61B 17/58 (2013.01); A61B 17/70 (2013.01)

(58) Field of Classification Search
CPC . A61B 17/72; A61B 17/7233; A61B 17/7208; A61B 17/88; A61B 17/8805; A61B 17/8816; A61B 17/58; A61B 17/86; A61B 17/8685; A61B 17/864; A61B 17/70
See application file for complete search history.

(56) References Cited

U.S. PATENT DOCUMENTS 2,328,270 A 8/1943 Daniel
2,724,573 A 11/1955 Lundquist
(Continued)

FOREIGN PATENT DOCUMENTS

AT 509852 A4 12/2011
AT 509852 B1 12/2011
(Continued)

OTHER PUBLICATIONS

US 7,273,482 B2, 09/2007, Dakin et al. (withdrawn)
(Continued)

*Primary Examiner* — Christopher J Beccia
(74) *Attorney, Agent, or Firm* — Fortem IP LLP

(57) ABSTRACT

Implantable intramedullary devices, and systems and methods related thereto, are provided which enable the delivery of a liquid material into an intramedullary channel. An implantable intramedullary device may include a delivery channel through which liquid material may be delivered through the device into the intramedullary channel. The intramedullary device may be adapted for coupling to a fluid delivery apparatus which delivers the liquid material into the delivery channel of the intramedullary device. Delivery catheters configured for insertion into implantable intramedullary devices are also disclosed. Liquid materials which may be delivered include bone cement, biologics, pharmacologic solutions, and other materials useful in conjunction with treatments involving intramedullary implants.

22 Claims, 10 Drawing Sheets

(56) References Cited

U.S. PATENT DOCUMENTS

| | | | |
|---|---|---|---|
| 3,371,725 A | 3/1968 | Wilhelm et al. |
| 4,098,351 A | 7/1978 | Alessio |
| 4,489,792 A | 12/1984 | Fahim et al. |
| 4,491,443 A | 1/1985 | Decaro |
| 4,605,348 A | 8/1986 | Decaro |
| 4,706,659 A | 11/1987 | Matthews et al. |
| 5,108,397 A | 4/1992 | White |
| 5,167,665 A | 12/1992 | McKinney |
| 5,234,435 A | 8/1993 | Seagrave |
| D346,218 S | 4/1994 | White |
| 5,300,071 A | 4/1994 | Browner et al. |
| 5,336,224 A | 8/1994 | Selman |
| 5,527,309 A | 6/1996 | Shelton |
| 5,527,310 A | 6/1996 | Cole et al. |
| 5,593,407 A | 1/1997 | Reis |
| 5,601,550 A | 2/1997 | Esser |
| 5,649,925 A | 7/1997 | Barbera |
| 5,879,352 A | 3/1999 | Filoso et al. |
| 5,944,719 A | 8/1999 | Leban |
| 5,993,454 A | 11/1999 | Longo |
| 6,209,886 B1 | 4/2001 | Estes et al. |
| 6,340,362 B1 | 1/2002 | Pierer et al. |
| 6,368,326 B1 | 4/2002 | Dakin et al. |
| 7,258,692 B2 | 8/2007 | Thelen et al. |
| 7,410,483 B2 | 8/2008 | Danitz et al. |
| 7,410,489 B2 | 8/2008 | Dakin et al. |
| 7,625,395 B2 | 12/2009 | Mueckter |
| 7,632,277 B2 | 12/2009 | Woll et al. |
| 7,785,325 B1 | 8/2010 | Milbank |
| 7,846,162 B2 | 12/2010 | Nelson et al. |
| 8,043,347 B2 | 10/2011 | Jiang et al. |
| 8,128,626 B2 | 3/2012 | Justin |
| 8,128,627 B2 | 3/2012 | Justin et al. |
| 8,157,803 B1 | 4/2012 | Zirkle et al. |
| 8,206,389 B2 | 6/2012 | Huebner et al. |
| 8,372,074 B2 | 2/2013 | Milbank |
| 8,409,257 B2 | 4/2013 | Edidin et al. |
| 8,439,916 B2 | 5/2013 | Coati et al. |
| 8,632,543 B2 | 1/2014 | Metzinger et al. |
| 8,961,516 B2 | 2/2015 | Nelson et al. |
| 9,060,809 B2 | 6/2015 | Tipirneni et al. |
| 9,144,506 B2 | 9/2015 | Phelps |
| 9,155,574 B2 | 10/2015 | Saravia et al. |
| 9,482,260 B1 | 11/2016 | Krause |
| 9,498,264 B2 | 11/2016 | Harshman et al. |
| 9,532,789 B2 | 1/2017 | Coope |
| 9,615,835 B2 | 4/2017 | Lam et al. |
| 9,839,435 B2 | 12/2017 | Meek et al. |
| 10,258,394 B2 | 4/2019 | Harshman et al. |
| 10,307,188 B2 | 6/2019 | Harshman et al. |
| 10,973,559 B2 | 4/2021 | Harshman et al. |
| 11,224,467 B2 | 1/2022 | Peterson et al. |
| 11,369,421 B2 | 6/2022 | Harshman et al. |
| 11,419,645 B2 | 8/2022 | Stinson et al. |
| 11,529,148 B2 | 12/2022 | Meek et al. |
| 11,826,262 B2 | 11/2023 | Glerum et al. |
| 11,832,856 B2 | 12/2023 | Meek et al. |
| 12,023,074 B2 | 7/2024 | Harshman et al. |
| 12,167,877 B2 | 12/2024 | Harshman et al. |
| 2002/0032444 A1 | 3/2002 | Mische |
| 2002/0077631 A1 | 6/2002 | Lubbers et al. |
| 2002/0087161 A1 | 7/2002 | Randall et al. |
| 2002/0198527 A1 | 12/2002 | Muckter |
| 2003/0078582 A1 | 4/2003 | Heggeness |
| 2003/0181982 A1 | 9/2003 | Kuslich |
| 2003/0187449 A1 | 10/2003 | McCleary et al. |
| 2003/0229351 A1 | 12/2003 | Tidwell et al. |
| 2004/0011565 A1 | 1/2004 | Lyon et al. |
| 2004/0024409 A1 | 2/2004 | Sand et al. |
| 2004/0050568 A1 | 3/2004 | Orozco |
| 2004/0102778 A1 | 5/2004 | Huebner et al. |
| 2004/0215191 A1 | 10/2004 | Kitchen |
| 2005/0055023 A1 | 3/2005 | Sohngen et al. |
| 2005/0082824 A1 | 4/2005 | Luettgen et al. |
| 2005/0085819 A1 | 4/2005 | Ellis et al. |
| 2005/0154390 A1 | 7/2005 | Matthis et al. |
| 2005/0165401 A1 | 7/2005 | Pack |
| 2006/0074421 A1 | 4/2006 | Bickley et al. |
| 2006/0264950 A1 | 11/2006 | Nelson et al. |
| 2007/0083204 A1 | 4/2007 | Sidebotham |
| 2007/0162132 A1 | 7/2007 | Messerli |
| 2007/0173834 A1 | 7/2007 | Thakkar |
| 2007/0208364 A1 | 9/2007 | Smith et al. |
| 2007/0233111 A1 | 10/2007 | Orbay et al. |
| 2008/0051786 A1 | 2/2008 | Jensen |
| 2008/0058722 A1 | 3/2008 | Von et al. |
| 2008/0077133 A1 | 3/2008 | Schulze |
| 2008/0077154 A1 | 3/2008 | Edwards et al. |
| 2008/0108989 A1 | 5/2008 | Parsell et al. |
| 2008/0161805 A1 | 7/2008 | Saravia et al. |
| 2008/0181740 A1 | 7/2008 | Waitszies |
| 2008/0195145 A1 | 8/2008 | Bonutti et al. |
| 2008/0234676 A1 | 9/2008 | Schulze et al. |
| 2008/0249628 A1 | 10/2008 | Altarac et al. |
| 2008/0269745 A1 | 10/2008 | Justin |
| 2008/0287951 A1 | 11/2008 | Stoneburner et al. |
| 2008/0294163 A1 | 11/2008 | Chou et al. |
| 2008/0294164 A1 | 11/2008 | Frank et al. |
| 2008/0319455 A1 | 12/2008 | Harris et al. |
| 2009/0024174 A1 | 1/2009 | Stark |
| 2009/0048672 A1 | 2/2009 | Essenmacher |
| 2009/0062797 A1 | 3/2009 | Huebner et al. |
| 2009/0149710 A1 | 6/2009 | Stefanchik et al. |
| 2009/0192512 A1 | 7/2009 | Sommers |
| 2009/0216232 A1 | 8/2009 | Buford et al. |
| 2009/0228008 A1 | 9/2009 | Justin et al. |
| 2009/0299343 A1 | 12/2009 | Rogers |
| 2010/0023010 A1 | 1/2010 | Nelson et al. |
| 2010/0076503 A1 | 3/2010 | Beyar et al. |
| 2010/0185290 A1 | 7/2010 | Compton et al. |
| 2010/0217333 A1 | 8/2010 | Mcshane et al. |
| 2010/0249832 A1 | 9/2010 | Thomas et al. |
| 2010/0249838 A1 | 9/2010 | Stopek et al. |
| 2010/0249854 A1 | 9/2010 | Thomas et al. |
| 2010/0249944 A1 | 9/2010 | Thomas et al. |
| 2010/0262239 A1 | 10/2010 | Boyden et al. |
| 2010/0286692 A1 | 11/2010 | Greenhalgh et al. |
| 2010/0298893 A1 | 11/2010 | Stucki |
| 2010/0318137 A1 | 12/2010 | Stucki et al. |
| 2010/0331842 A1 | 12/2010 | Milbank |
| 2011/0015684 A1 | 1/2011 | Belcheva et al. |
| 2011/0028974 A1 | 2/2011 | Chemello |
| 2011/0040282 A1 | 2/2011 | Uihlein |
| 2011/0046746 A1 | 2/2011 | Rabiner et al. |
| 2011/0087227 A1 | 4/2011 | Mazur et al. |
| 2011/0098757 A1 | 4/2011 | Schelling |
| 2011/0098816 A1 | 4/2011 | Jacob et al. |
| 2011/0098817 A1 | 4/2011 | Eckhardt et al. |
| 2011/0119815 A1 | 5/2011 | Paulson et al. |
| 2011/0144643 A1 | 6/2011 | Lorenz et al. |
| 2011/0144645 A1 | 6/2011 | Saravia et al. |
| 2011/0144703 A1 | 6/2011 | Krause et al. |
| 2011/0153454 A1 | 6/2011 | Dunn et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196435 A1 | 8/2011 | Forsell |
| 2011/0218644 A1* | 9/2011 | Meridew .......... A61M 5/14276 623/23.15 |
| 2011/0230966 A1 | 9/2011 | Trieu |
| 2011/0238181 A1 | 9/2011 | Trieu |
| 2011/0264229 A1 | 10/2011 | Donner |
| 2011/0288598 A1 | 11/2011 | Moed et al. |
| 2011/0306975 A1 | 12/2011 | Kaikkonen et al. |
| 2011/0319944 A1 | 12/2011 | Borodic |
| 2012/0010617 A1 | 1/2012 | Ramos |
| 2012/0065638 A1 | 3/2012 | Moore |
| 2012/0078252 A1 | 3/2012 | Huebner et al. |
| 2012/0078311 A1 | 3/2012 | Huebner et al. |
| 2012/0083847 A1 | 4/2012 | Huebner et al. |
| 2012/0083895 A1 | 4/2012 | Conway et al. |
| 2012/0101533 A1 | 4/2012 | Purcell et al. |
| 2012/0101576 A1 | 4/2012 | Dewey et al. |
| 2013/0006145 A1 | 1/2013 | Toomey et al. |

(56) References Cited

U.S. PATENT DOCUMENTS

| | | | |
|---|---|---|---|
| 2013/0006245 A1 | 1/2013 | Stoneburner et al. | |
| 2013/0012942 A1 | 1/2013 | Nelson et al. | |
| 2013/0131678 A1 | 5/2013 | Dahners | |
| 2013/0144348 A1 | 6/2013 | Schwappach | |
| 2013/0325007 A1 | 12/2013 | Beyar et al. | |
| 2014/0114312 A1 | 4/2014 | Krause | |
| 2014/0296853 A1 | 10/2014 | Wolter | |
| 2014/0309636 A1 | 10/2014 | Meek et al. | |
| 2014/0358146 A1 | 12/2014 | Meek et al. | |
| 2015/0012051 A1 | 1/2015 | Warren et al. | |
| 2015/0038970 A1 | 2/2015 | Coope | |
| 2015/0157370 A1 | 6/2015 | Gross | |
| 2015/0257800 A1* | 9/2015 | Harshman | A61B 17/7208 |
| | | | 606/62 |
| 2015/0297245 A1 | 10/2015 | Lam et al. | |
| 2017/0014170 A1 | 1/2017 | Fallin et al. | |
| 2017/0020585 A1 | 1/2017 | Harshman et al. | |
| 2017/0049460 A1 | 2/2017 | Coope | |
| 2017/0164953 A1 | 6/2017 | Lam et al. | |
| 2017/0238977 A1 | 8/2017 | Harshman et al. | |
| 2018/0092681 A1 | 4/2018 | Lutz | |
| 2018/0296227 A1 | 10/2018 | Meek et al. | |
| 2019/0120282 A1 | 4/2019 | Krause | |
| 2019/0231401 A1 | 8/2019 | Harshman et al. | |
| 2019/0282280 A1 | 9/2019 | Harshman et al. | |
| 2020/0038646 A1* | 2/2020 | Sweeney | A61M 39/0247 |
| 2020/0054372 A1 | 2/2020 | Stinson et al. | |
| 2020/0138492 A1 | 5/2020 | Kavanagh | |
| 2021/0220027 A1 | 7/2021 | Harshman et al. | |
| 2021/0322070 A1 | 10/2021 | Koch et al. | |
| 2021/0353338 A1 | 11/2021 | Meek et al. | |
| 2021/0386465 A1 | 12/2021 | Thaler et al. | |
| 2022/0287744 A1 | 9/2022 | Harshman et al. | |
| 2022/0354549 A1 | 11/2022 | Stinson et al. | |
| 2023/0157708 A1 | 5/2023 | Meek et al. | |
| 2023/0404636 A1 | 12/2023 | Whittaker et al. | |
| 2024/0081880 A1 | 3/2024 | Meek et al. | |
| 2024/0307098 A1 | 9/2024 | Harshman et al. | |
| 2025/0064489 A1 | 2/2025 | Harshman et al. | |
| 2025/0325281 A1 | 10/2025 | Meek et al. | |

FOREIGN PATENT DOCUMENTS

| | | | |
|---|---|---|---|
| CA | 2725324 | A1 | 11/2009 |
| CN | 2662839 | Y | 12/2004 |
| CN | 2699846 | Y | 5/2005 |
| CN | 101208053 | A | 6/2008 |
| CN | 101633119 | A | 1/2010 |
| CN | 101636119 | A | 1/2010 |
| CN | 102793579 | A | 11/2012 |
| CN | 103025257 | A | 4/2013 |
| CN | 103200887 | A | 7/2013 |
| CN | 103813764 | A | 5/2014 |
| CN | 104203132 | A | 12/2014 |
| CN | 104837425 | A | 8/2015 |
| CN | 104203132 | B | 8/2017 |
| CN | 107106217 | A | 8/2017 |
| CN | 112955087 | A | 6/2021 |
| EP | 0078619 | A2 | 5/1983 |
| EP | 1941838 | A1 | 7/2008 |
| EP | 2779928 | A1 | 9/2014 |
| EP | 3326558 | A1 | 5/2018 |
| EP | 3206608 | A4 | 7/2018 |
| EP | 3522803 | A1 | 8/2019 |
| EP | 3866712 | A1 | 8/2021 |
| GB | 1494553 | A | 12/1977 |
| WO | 2007009123 | A2 | 1/2007 |
| WO | 2008116175 | A2 | 9/2008 |
| WO | 2008120877 | A1 | 10/2008 |
| WO | 2009143374 | A2 | 11/2009 |
| WO | 2010124230 | A1 | 10/2010 |
| WO | 2011067668 | A1 | 6/2011 |
| WO | 2011119815 | A2 | 9/2011 |
| WO | 2011153454 | A2 | 12/2011 |
| WO | 2012107913 | A2 | 8/2012 |
| WO | 2013063145 | A1 | 5/2013 |
| WO | 2013071432 | A1 | 5/2013 |
| WO | 2014075165 | A1 | 5/2014 |
| WO | 2014075184 | A1 | 5/2014 |
| WO | 2015134750 | A1 | 9/2015 |
| WO | 2016061173 | A1 | 4/2016 |
| WO | 2018067888 | A1 | 4/2018 |
| WO | 2020077457 | A1 | 4/2020 |
| WO | 2020081855 | A1 | 4/2020 |

OTHER PUBLICATIONS

"UT Southwest Medical Surgeons Market Pelvic Fracture Device", Accessed at http://www.texasbusiness.com/ut-southwest-medical-surgeons-market-pelvic-fracture-device-cms-4418, Texas Business. com, Apr. 22, 2011, pp. 1-5.

Barry, et al., "Flexible intramedullary nails for fractures in children", Aspects of Current Management, vol. 86-B, No. 7, British Editorial Society of Bone and Joint Surgery, Sep. 2004, pp. 1-7.

Cheung, et al., "A New Halo-Pelvic Apparatus", Spine, vol. 28, No. 3, pp. 305-308.

Ganz, et al., "Surgical dislocation of the adult hip", The Journal of Bone and Joint Surgery (Br), vol. 83-B, No. 8, British Editorial Society of Bone and Joint Surgery, Nov. 2004, pp. 1119-1124.

Griffin, et al., "Vertically Unstable Pelvic Fractures Fixed with Percutaneous Iliosacral Screws: Does Posterior Injury Jattem Prediction Fixation Failure?", Journal of Orthopedic Trauma, vol. 17, No. 6, Lippincott Williams, and Wilkins, Inc., Jan. 2006, pp. 399-405.

Miller, et al., "Variations in Sacral Morphology and Implications for Iliosacral Screw Fixation", Journal of the American Academy of Orthopaedic Surgeons, vol. 20, No. 1, American Academy of Orthopaedic Surgeons, Jan. 2012, pp. 8-16.

Novick, "Pelvic Fractures/Acetabular Fractures", Hospital for Special Surgery, Mar. 30, 2006, HSS.edu, Mar. 30, 2006, pp. 1-9.

Novick, "Pelvic Fractures/Acetabular Fractures—An Interview with Dr. David L. Helfet", Hospital for Special Surgery, accessed at http://www.hss.edu/conditions-pelvic-acetabulum-fractures.asp, Mar. 30, 2006, 10 Pages.

Starr, "Fractures of the Pelvic Ring", in Rockwood & Green's Fractures in Adults 6th Edition, Chapter—41, accessed on Feb. 4, 2014, Lippincott Williams & Wilkins, pp. 1-40.

Starr, et al., "Superior Pubic Ramus Fractures Fixed With Percutaneous Screws: What Predicts Fixation Failure?", Journal of Orthopaedic Trauma, vol. 22, No. 2, Lippincott Williams and Wilkins, Feb. 2008, pp. 81-87.

Vaidya, R. , et al., "Complications of Anterior Subcutaneous Internal Fixation for Unstable Pelvis Fractures: A Multicenter Study", Clinical Orthopaedics and Related Research, vol. 470, No. 8, Springer, Aug. 2012, pp. 1-8.

* cited by examiner

DEVICES, SYSTEMS, AND METHODS OF USE FOR DELIVERY OF MATERIALS IN COMBINATION WITH INTRAMEDULLARY DEVICES

CROSS-REFERENCE TO RELATED APPLICATION(S)

The present application claims the benefit of priority to U.S. Provisional Application No. 63/267,590, filed Feb. 4, 2022, which is incorporated by reference herein in its entirety.

BACKGROUND

Various treatments of bone conditions may involve the use of implantable devices such as bone screws, rods, plates, and the like. For example, large bone fractures such as pelvic and hip fractures frequently require the use of implantable intramedullary devices such as rods and/or screws extending at least partially through or within an intramedullary channel within the bone. In some cases, surgical tools such as reamers are used to create such intramedullary channels prior to implantation of the intramedullary device.

Pelvic fractures involve particularly complex repair procedures, due in part to their curved, saddle-like shape. To repair a fractured pelvis, the surgeon must insert rods or screws across the fracture(s) to immobilize the bone fragments and allow them to grow back together. The straight, rigid rods and screws conventionally used for fracture repairs frequently are unsuited for the pelvis due to their inability to conform to the complex curvature of the bone, or to follow a curved intramedullary channel formed in bone.

There is a need for improved devices, systems, and methods for treating fractures in curved bones.

SUMMARY

Some embodiments of an implantable intramedullary device according to the present technology includes a device body having a proximal portion and an elongate portion that can pass through an intramedullary pathway within the bone, the elongate portion having a first end coupled to the proximal portion and a second end opposite the first end. The proximal portion may have a connection portion configured for connecting to an inserter device for inserting the intramedullary device into an intramedullary channel in the bone. A distal portion may be coupled to, or integrally formed with, the second end of the elongate portion.

In some embodiments, the elongate portion is flexible or shapable into a curved shape so as to be capable of following a curved intramedullary pathway in the bone. In such embodiments, the elongate portion will be lockable into a rigid state so as to maintain a desired curved shape while implanted in the bone. Such embodiments may further include a locking mechanism which can be actuated in the proximal portion for locking the elongate portion in the rigid state. In some embodiments, the locking mechanism is configured to be coupled to an actuator of an inserter device which can be actuated to lock the elongate portion in the rigid state.

The intramedullary device may further include a delivery channel extending through at least one of the proximal portion and the elongate portion, an inlet port in the proximal portion in communication with the channel, and one or more exit ports along the axial length of the proximal portion, elongate portion, and/or distal tip configured for delivery of a viscous liquid material such as bone cement, therapeutic agents such as biologics, drugs, or other materials. Such materials may be delivered for therapeutic purposes such as inhibiting or treating infection, promoting bone growth, or treating other conditions, for filling gaps within the bone, or for attaching or adhering an intramedullary implant to bone or to a prosthetic device (e.g. joint replacement prosthesis or other implant), as well as other purposes.

Some embodiments of the intramedullary implant may further include a connector, valve, or other fitting on the proximal portion which is in fluid communication with the inlet port and configured for connection to a syringe, injector, catheter, or other fluid delivery apparatus for delivering the bone cement, biologics or other materials through the inlet port and into the delivery channel. In some embodiments, the delivery apparatus is capable of delivering a viscous liquid material such as bone cement at sufficiently high pressures to pass through the delivery channel and exit ports into the intramedullary space. In some embodiments the delivery apparatus is configured to deliver materials having a viscosity in the range of about 10-1000 cP, 10-200 cP, or 10-100 cP, at pressures of no more than about 200-300 psi.

In some embodiments, the fluid delivery apparatus may include a delivery tube or catheter which may be inserted through the inlet port into the delivery channel and advanced a desired distance through the proximal portion, elongate portion, and/or distal portion. In this way, the liquid material may be directed to a selected one or more exit ports along the length of the intramedullary device, or to a location distally of the intramedullary device, so as to target desired locations within the intramedullary space to which the liquid material may be delivered. In such embodiments, the fitting, inlet port, and/or delivery channel can be configured to slidingly receive such tube or catheter and provide a fluid tight seal therewith to inhibit leakage of the liquid material through the inlet port under high pressures.

The present technology further provides an intramedullary treatment system comprising an intramedullary device and a fluid delivery apparatus as described above. The intramedullary treatment system may further include a container of a liquid material such as bone cement, biologic, drug, or other material, the container being adapted for fluid connection to the delivery apparatus. The intramedullary treatment system may alternatively or additionally include containers or packages of one or more components in a liquid or dry form, which can be combined with other compounds, agents, or media by the user to create the desired liquid material at the time of treatment.

In further embodiments, the intramedullary treatment system may include an inserter device for inserting the intramedullary device in bone. The inserter device may include a mechanism for locking the intramedullary device in a rigid state after insertion. In some embodiments, the inserter device may be configured to be fluidly and/or mechanically coupled to the fluid delivery apparatus and may be configured to direct liquid material into the delivery channel of the intramedullary device. Alternatively, the inserter device may include an introduction channel to receive a tube, catheter, or other delivery component of the fluid delivery apparatus and directing such component and/or liquid material into the delivery channel.

A catheter embodiment for delivering bone cement or biologics through the intramedullary implant can include a polymer tube sized appropriately to the channel in the intramedullary implant. One end of the tube may have any one of a variety of connectors to couple to a syringe of bone cement or biologics. The other end may have an additional connector to couple to a mating connector on the intramedullary implant. Alternatively, the end of the catheter may be open to deliver material through the end at a desired location inside the intramedullary implant. Additionally, the catheter may contain radiopaque markers or external markings to indicate depth of placement of the catheter with respect to the intramedullary implant or patient tissue. Moreover, the catheter may contain a number of side-holes in various quantities or patterns to deliver bone cement or biologics at multiple locations along the inside of the intramedullary implant.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology is directed towards implantable intramedullary devices, and systems and methods related thereto, which enable delivery of liquid materials into an intramedullary channel in a bone. Delivery of liquid materials into the intramedullary channel in conjunction with the intramedullary implant may enhance fixation of the implants or immobilization of the bones, promote bone growth, ward off infection, reduce pain, inhibit or treat diseases, as well as serve other therapeutic purposes. Conventional intramedullary devices do not have such capability, as access into the intramedullary channel is blocked by the device itself.

The devices and systems disclosed herein allow therapeutic and other materials to be delivered into an intramedullary space before an intramedullary device is implanted, or while the intramedullary device is implanted, in order to enhance treatment of fractures and other bone conditions. The intramedullary devices of the present technology may either be straight, rigid devices, or flexible devices configured to follow a curved intramedullary channel then fixed in a rigid state once in an implanted position in the bone. In some embodiments, the present technology is configured to deliver liquid materials having high viscosity, such as bone cement, along with less viscous materials, such as biologics and pharmacologic solutions.

"Implantable," as used herein, refers to anything intended to be implanted, i.e. fixed to or within a patient's body and left behind for an extended period of time (e.g., in excess of a few days or weeks), and in many cases, permanently. At least in the case of intramedullary devices, "implantable" is further intended to mean devices which are implanted through an incision in the skin and are disposed at least partially in an intramedullary space within a bone, and the devices remain in the bone after the incision is closed, with the entire device remaining under the skin.

Figures 1A, 1B:
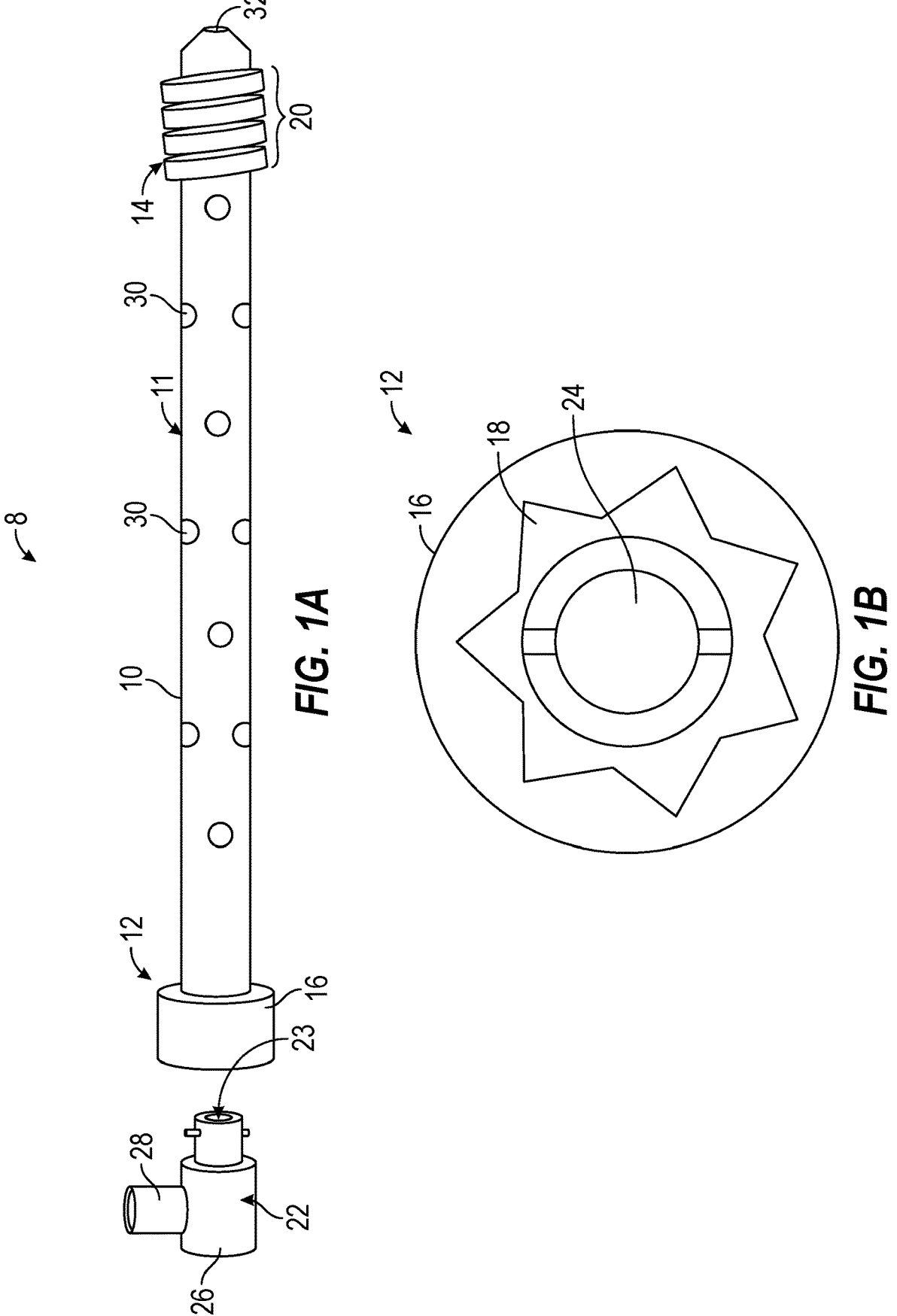
FIGS. 1A-1B are side elevation and end view, respectively, of an implantable intramedullary device according to several embodiments of the present technology.

FIG. 1A shows a device 8 configured to be implanted in an intramedullary channel of a bone, according to several embodiments of the present technology. The device 8 comprises an elongate body 10 having a proximal portion 12, a distal portion 14, and an elongate portion 11 positioned between the proximal and distal portions 12, 14. The elongate body 10 can comprise a sidewall defining a lumen 24 (see FIG. 1B) extending therethrough and including a plurality of exit ports 30 in fluid communication with the lumen 24. An opening 32 at the distal end of the distal portion 14 can also be in fluid communication with the lumen 24. The distal portion 14 of the elongate body 10 can further include a threaded region 20 for securing the device 8 in the bone.

The proximal portion 12 can be configured to be coupled to an inserter device for inserting the device 8 into an intramedullary channel in a bone. The proximal portion 12 can include, for example, a head 16 having a driver receptacle 18. As shown in the axial cross-sectional view of the head 16 in FIG. 1B, in some embodiments the driver receptable 18 can have a cross-sectional shape comprising a star. Other shapes are possible, such as a square, circle, triangle, undefined shape, polygon, and many others. In some embodiments, the proximal portion 12 is configured to be coupled to a fitting 22 (e.g., via a luer lock or other sealable connection methods). The fitting 22 can be configured to fluidly seal with the proximal portion 12 and includes an inner passage 23 that communicates with the lumen 24 within the elongate body 10. The fitting 22 has a proximal end portion 26 configured to be coupled with a fluid delivery apparatus (not shown). Alternatively or additionally, the fitting 22 may have a sidearm 28 having an inner lumen (not shown) communicating with the inner passage 23 of the fitting 22. Either or both proximal end portion 26 and sidearm 28 may have a coupling (e.g., a luer lock or other sealable connection method) for coupling to a fluid delivery tube or apparatus.

The device 8 can be constructed of a biocompatible rigid material suitable for implantation in bone, such as stainless steel or titanium. The elongate body 10 can have sufficient strength and bending stiffness as required for repair of bone fractures including, e.g., fractures of the pelvis, femur, tibia, humorous, spine, and other bones. The principles of the present technology may also be applied to other implantable devices for other purposes as well. The elongate body 10 can have a length and diameter selected for the particular bone and nature of the treatment to be executed.

Figures 2A, 2B:
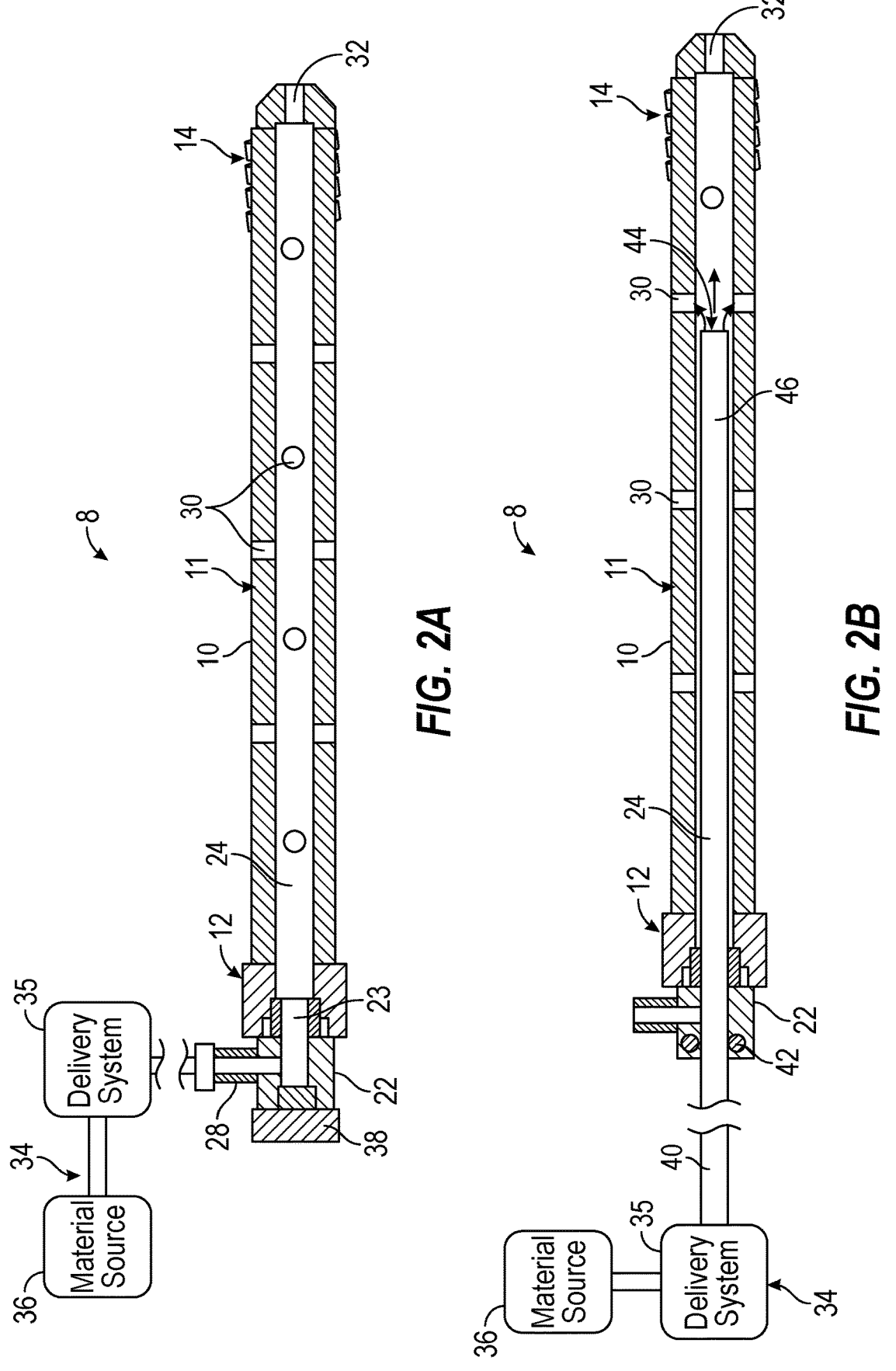
FIGS. 2A-2B are side cross-sectional views of different implantable intramedullary devices according to several embodiments of the present technology.

The liquid material can be delivered into the lumen 24 of the elongate body 10 directly through the fitting 22 (when coupled to the device 8), or through an additional device configured to be received through the fitting 22 and the lumen 24. For example, as shown in FIG. 2A, the present technology can include a fluid delivery system 34 comprising a fluid delivery device 35 and a material source 36. The fluid delivery device 34 may comprise, for example, a syringe, power injector, a pump, or other fluid delivery mechanism. The liquid material can comprise bone cement and/or a therapeutic agent (e.g., biologics, antibiotics, pharmacologic agents, or other materials useful in the relevant treatment).

Following insertion of the device 8 into an intramedullary channel in a bone, the liquid material is delivered through the lumen 24 and exit ports 30 into the intramedullary channel. The fluid delivery device 35 can be configured to be coupled to the sidearm 28 of the fitting 22 and deliver a liquid material from the material source 36 through the inner passage 23 of the fitting 22 into the lumen 24 of the elongate body 10. In some embodiments, the fluid delivery system 34 can include a cap 38 that is configured to be coupled to the proximal end of the fitting 22 to seal the proximal opening of the inner passage 23. In embodiments having no sidearm 28, the fluid delivery device 35 may be connected to the proximal end portion 26 of the fitting 22 in place of the cap 38.

As shown in FIG. 2B, in some embodiments the fluid delivery system 34 comprises a tube or catheter 40 (hereinafter referred to as catheter 40) coupled to the fluid delivery device 35 and configured for insertion through the fitting 22 into the lumen 24. Optionally the fitting 22 may include a seal 42 in the inner passage 23, such as an O-ring or other suitable means for providing a fluid seal around tube or catheter 40. The catheter 40 can have at least one axial lumen therein extending to a delivery port 44 at its distal end portion 46 through which liquid material can be delivered into the lumen 24. The catheter 40 is slidable within the lumen 24 such that the distal end portion 46 may be positioned at a selectable axial location therein. In this way, the delivery port 44 may be positioned near a selected one or more of the exit ports 30 so that the liquid material may be directed preferentially through such exit port(s). In some embodiments, the catheter 40 is configured to fit snugly but slidably within the lumen 24 such that liquid material is inhibited from flowing proximally through the lumen 24 from the delivery port 44 of the catheter 40. In other embodiments, the catheter 40 has a diameter somewhat smaller than the inner diameter of the lumen 24 to allow the liquid material to flow proximally, as well as distally and laterally, from the delivery port 44.

The catheter 40 may be either rigid or flexible, and may have various embodiments including a metal hypotube, a polymeric tube or cannula, a single- or multi-lumen catheter, or other suitable tubular delivery device. The catheter 40 can be sized and configured for insertion into the lumen 24 and suitable for delivering the relevant liquid material into the intramedullary channel at the desired pressures and flow rates. In some embodiments, highly viscous materials such as bone cement may be delivered, in which case the catheter

40 will be configured to withstand the higher pressures required to deliver such materials through a channel the size of the lumen 24 over the desired distance in the intramedullary channel. In such embodiments, the wall of the catheter 40 may be reinforced with a braided material or other suitable reinforcing means. In some embodiments, the catheter 40 has a diameter of about 6-12 French, and is configured to withstand delivery pressures of up to about 300 psi.

The catheter 40 can optionally include radiopaque markers and/or external visual markings to allow radiographic and/or direct visualization of the catheter when inserted into lumen 24. Radiopaque dye can also be infused in the material used to construct the catheter 40 or in a coating thereon. Radiopaque markings at the distal end portion and/or along the length of catheter 40 allow the position of the catheter 40 to be radiographically visualized relative to the intramedullary device and/or the surrounding bone. This facilitates placement of the catheter 40 at the desired site of delivery of the liquid material. In some embodiments, the catheter 40 may be visualized while it is inserted within the lumen 24 to position the distal port near a selected one or more exit ports 30, or in the intramedullary channel distally of the device 8.

Optionally, the catheter 40 may have one or more balloons attached near its distal end portion, and an inflation lumen in addition to a liquid delivery lumen. The inflation lumen communicates with the interior of the balloon(s) to enable balloon inflation. Such balloons may be used to occlude a selected location(s) in the lumen 24 of the intramedullary device 8 so as to block proximal or distal flow of the liquid material, or to isolate a region of the lumen 24 to which liquid material is to be directed. Such a balloon may also be advanced distally of device 8 and inflated within the intramedullary channel, e.g., to widen the channel to accommodate bone cement or other materials, or to occlude the intramedullary channel so as to block material from flowing distally. In such cases, catheter 40 may have an exit port in a sidewall thereof, either distally or proximally of the balloon, which communicates with the liquid delivery lumen therein.

In some embodiments, the catheter 40 may comprise a single or multi-lumen polymer tube sized for insertion in the reamed channel in a bone which is typically created prior to insertion of the intramedullary device 8. The catheter 40 may be advanced over a guidewire into the intramedullary channel and used to deliver bone cement, biologics, or other materials inside the intramedullary channel through exit ports on the end or sides of the catheter prior to insertion of the device 8.

The catheter 40 may include one or more balloons at its end or any other location thereon to limit the flow of liquid material to a specific area. Moreover, the catheter 40 can include radiopaque markers and/or external markings to allow radiographic visualization of the catheter within the bone and navigating to the desired site of delivery of the liquid material.

The fluid delivery system 34 and/or fluid delivery device 35 can be configured to deliver a desired liquid material into the device 8 and/or directly into the intramedullary channel. In some embodiments, the liquid material may comprise a viscous material such as low viscosity bone cement having a viscosity in the range of about 10-100 cP, or in some cases higher. In order to deliver such material through the lumen 24, which will typically have an inner diameter in the range of about 2-4 mm, the fluid delivery device can be configured to deliver the liquid material at a pressure of at least about 100 psi, 200 psi, or 300 psi. In some embodiments, the fluid delivery system 34 and/or fluid delivery device 35 comprises a power injector, electrically or pneumatically powered, capable of delivering highly viscous liquid material at these pressures. The material source 36, and all of the tubing, reservoirs, material containers, etc. associated with the fluid delivery system 34, as well as the catheter 40, will be appropriately constructed to withstand these pressures. In some embodiments, the catheter 40 includes a reinforced wall with, e.g., a braided material, a coil, etc. embedded therein.

Additionally or alternatively, the fluid delivery system 34 and/or fluid delivery device 35 may be configured to deliver less viscous liquid materials such as biologics or pharmacologic solutions, and may comprise a syringe, a fluid pump, or other suitable delivery means.

Figure 3B:
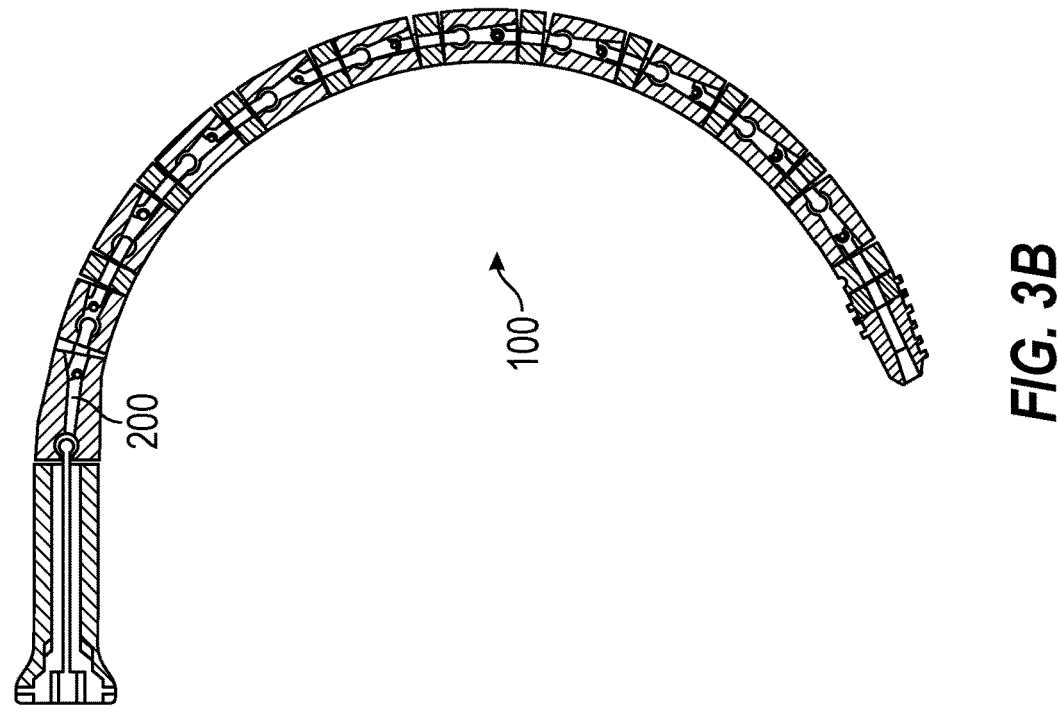
FIGS. 3A-3B are side elevation and side cross-section, respectively, of an implantable intramedullary device according to several embodiments of the present technology.
Figure 3A:
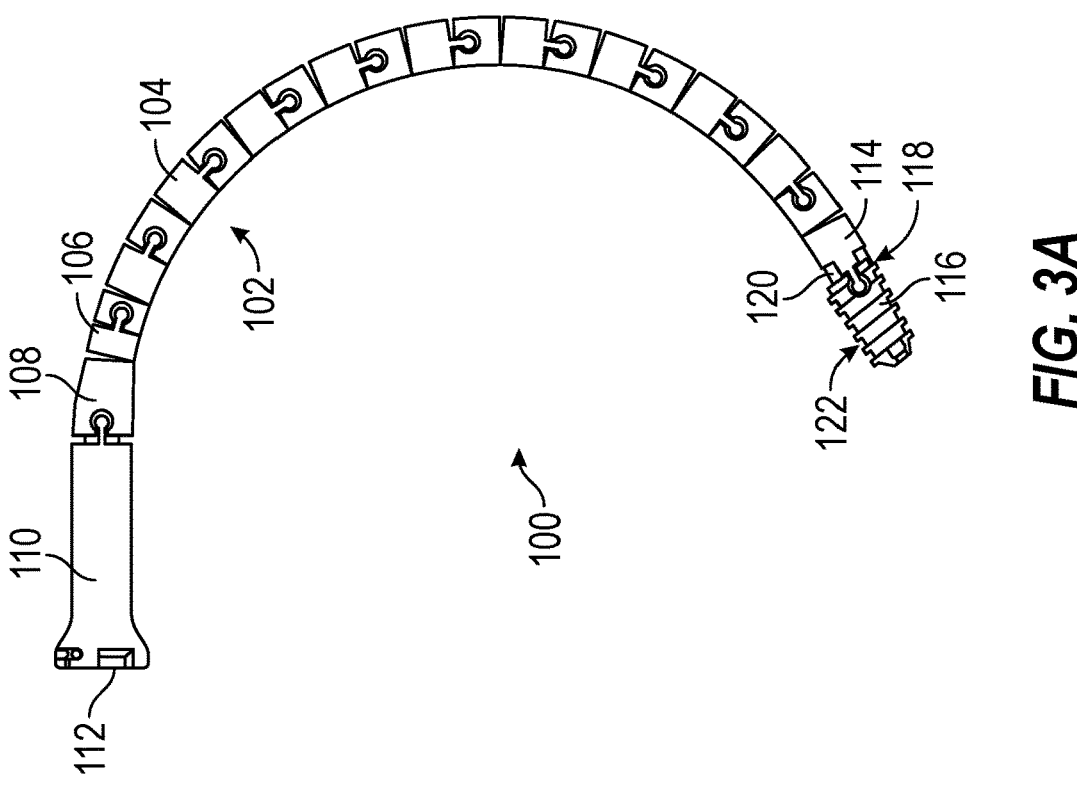

FIGS. 3A and 3B show an intramedullary device 100 (or "device 100") configured in accordance with several embodiments of the present technology. The device 100 comprises a selectively rigidizable elongate body 102 configured to follow a curved intramedullary channel in a bone. In several of such embodiments, an intramedullary device 100 is configurable in a curved or straight shape. Although shown as being shaped in a single curve in a single plane, the device may be configured to include multiple curves, where one of the curves is in a different plane than at least another one of the curves. The device 100 includes a body 102 formed from one or more body beads 104, one or more spacer beads 106, one or more transition beads 108, a proximal housing 110, a proximal lock 112, one or more anchor beads 114, a distal bead (hereinafter "distal end portion") 116, and flexible members (not shown in FIGS. 3A and 3B). Different combinations and numbers of body and spacer beads 104 and 106 can be utilized to create different-length devices from, e.g., 110 millimeters (mm) to 210 mm long. Longer or shorter devices can also be created for bone fixation in longer or shorter intramedullary bone pathways.

The body beads 104 are further described below in conjunction with FIGS. 4A-7B. Other than its length, each spacer bead 106 is similar to a body bead 104. Each transition bead 108 is configured to couple the proximal portion 110 to the body 102. The proximal portion 110 includes a proximal lock 112, which is a mechanism configured to cause the remaining portion (e.g., the body 104 and the distal portion 116) of the device 100 to be flexible while the proximal lock is in an unlocked state, and which is configured to cause the remaining portion of the device 100 to be rigid while the proximal lock is in a locked state. The anchor bead 114 is configured to couple the distal portion 116 to the body 102, and the anchor bead closest to the distal end includes cable receptacles, also called cable bores, configured to receive the ends of the flexible members. The distal portion 116 includes relatively sharp threads 122 configured to engage bone by being screwable into bone.

The flexible members (not shown in FIGS. 3A and 3B) extend through internal lumens from the anchor bead 114 to, and into, the proximal portion 110. The flexible members can comprise metal cables, wire, fibers, plastic or other fibers (e.g., carbon fiber). While the proximal lock 112 is in an unlocked state, the flexible members are free to slide relative to one another in an axial dimension (length dimension of the device 100) and to acquire a respective bend radius while the device 100 is in its flexible state and curved. While the proximal lock 112 is in a locked state, the lock prevents the flexible members from sliding relative to one another in an axial dimension, and the flexible members are configured to maintain, rigidly, the device 100 in a shape (such as a curved shape) that the device 100 acquired while it was in its flexible configuration. In some embodiments, the device 100 includes four flexible members, although the device 100 can include fewer than, or more than, four cables.

The distal ends of the flexible members can be coupled to a stabilizing bead, end cap, and/or other structure along the length of the device (e.g., by press fitting, welding, etc.) to keep the distal ends of the flexible members from "slipping through" the most-distal anchor bead 114. In FIGS. 3A and 3B, the distal ends of the flexible members are coupled to a bead 120. The bead may be made from any suitable material, such as steel or another metal, or from a polymer. Furthermore, although not shown in FIG. 3A, the proximal ends of the flexible members (which are, in FIG. 3A, hidden from view by a housing of the proximal portion 110) may also be fitted with a stabilizing bead, end cap, and/or other structure that are the same as, or that are similar to, bead 120.

Referring to FIG. 3B, the device 100 also includes a delivery channel 200 (also called a guidewire or central opening or through hole) along a longitudinal axis of the device 100, according to some embodiments. The delivery channel 200 is configured to receive a guidewire (not shown) such that during an implantation procedure, a surgeon can slide the device 100 over a guidewire that was previously inserted into an intramedullary channel of a fractured bone. Typically, after the device 100 is implanted, the surgeon removes the guidewire from the delivery channel 200. The delivery channel 200 may also be configured to receive a liquid material and/or a fluid delivery catheter (such as fluid delivery catheter 40), as detailed herein.

Figure 4B:
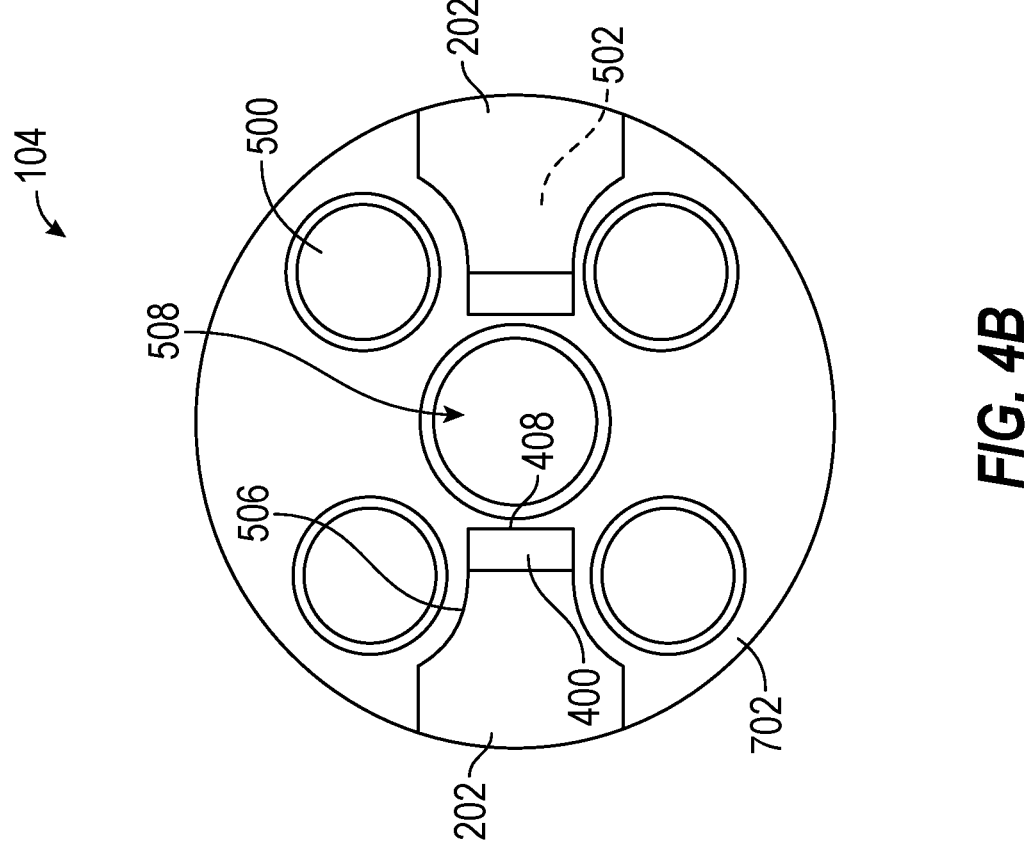
FIGS. 4A-4B are perspective and end views, respectively, of a body bead configured for use with the implantable intramedullary devices of the present technology.
Figure 4A:
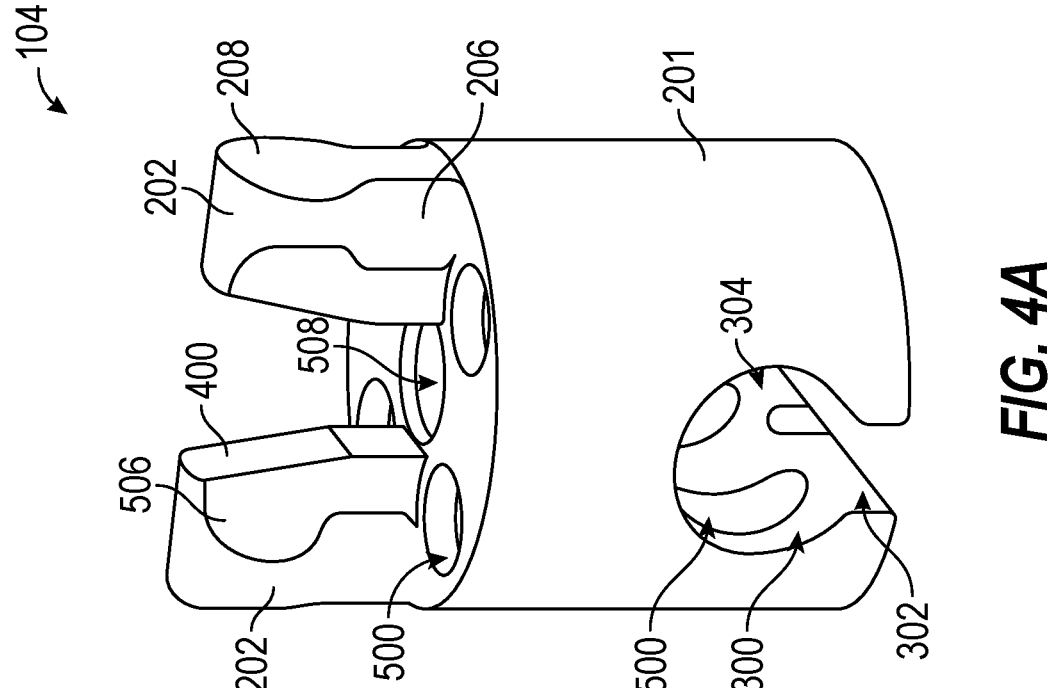

FIGS. 4A and 4B are perspective and top views, respectively, of an example body bead 104. Each body bead 104 can include a base 201, two tabs 202, one pocket 300, four holes 500 for receiving one of the flexible members therethrough, and a central through hole 508. When the body beads 104 are assembled in the device 100, the central through holes 508 can be generally axially aligned so as to collectively form the delivery channel 200 (see FIG. 3B) extending through all or most of the length of device 100. The through holes 500 can be evenly spaced (e.g., approximately 90 degrees apart) around a periphery of the base 201, and the center through hole 508 can be centered within the base. Other spacings are possible. The through holes 500 are configured to allow free axial movement of the flexible members and beads 104 with respect to each other while the device 100 is unlocked and, therefore, is in a flexible configuration. The body bead 104 can be made from any suitable material, such as surgical steel, titanium, another metal, or a polymer (e.g., PEEK or others).

Each of the tabs 202 can have a "lollipop" shape, with a stem, or neck, 206 and a head 208. Each of the tabs 202 has a respective chamfered surface 400 that begins at a height spaced above the top surface of the base 201. The chamfered surface 400 facilitates bending of the device 100 while a guidewire is present within the delivery channel 200. Each tab 202 has curved sidewalls 506, which allow rotation and other movement of the bead 104 relative to the other beads with reduced or no interference with the flexible members that extend through the through holes 500.

The pocket 300, like the tabs 202, can have a lollipop shape, with a stem, or neck, 302 and a head 304, and extends, with its full cross-sectional dimensions, all the way through the base 201 of the bead 104. The pocket 300 can be configured to receive the tabs 202 of another bead 104 in a manner that allows the two beads to rotate relative to one another so that the device 100 can bend and curve.

Figures 5A, 5B:
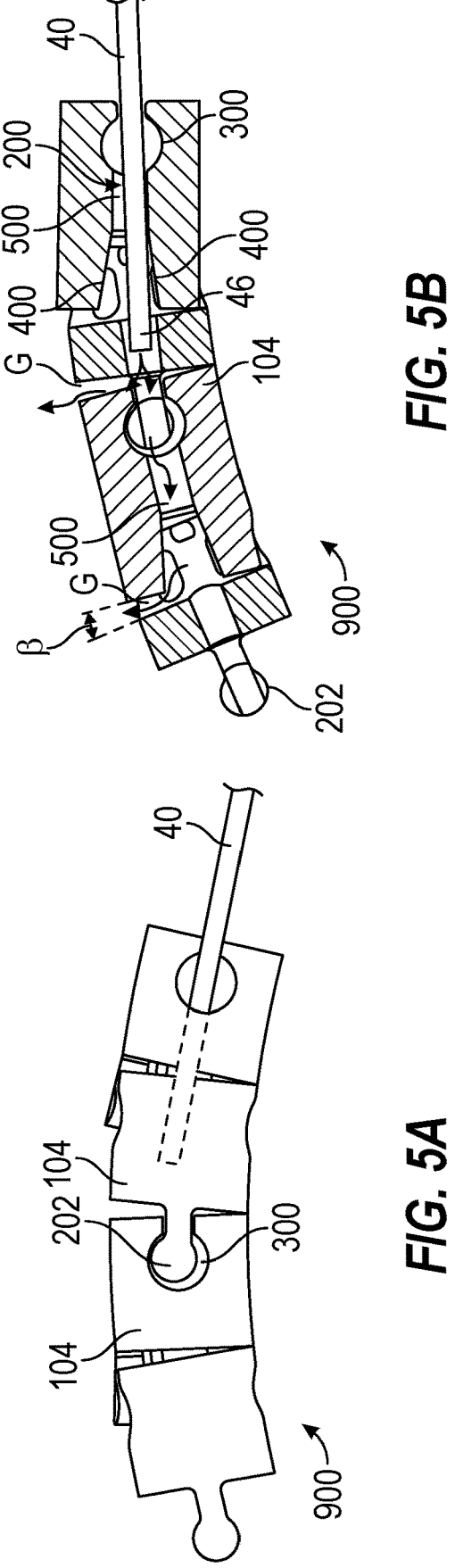
FIGS. 5A-5B are side elevation and side cross-section views, respectively, of a portion of an implantable intramedullary device of the present technology incorporating the body bead of FIGS. 4A-4B.

FIGS. 5A and 5B illustrate a segment 900 of the device 100 locked in a curved shape and positioned within an intramedullary channel of a bone (not shown). A flexible fluid delivery catheter (e.g., catheter 40, etc.) is shown inserted into the delivery channel 200. The distal end portion 46 of the catheter 40 may be positioned at a selected axial location within the delivery channel 200 using radiographic visualization. Liquid material, such as bone cement or other material, may then be delivered through the catheter 40 into the delivery channel 200. Gaps G between adjacent body beads 104 can provide exit ports along the length of device 100 through which the liquid material flows from the delivery channel 200 into the intramedullary channel. Advantageously, bone cement may be delivered in this fashion so that it hardens both within and around device 100 as well as in gaps G, thereby anchoring the device 100 in the intramedullary channel, assisting in locking the device 100 in its curved shape, and adding greater stiffness to the device 100 to immobilize the fractured bone.

Figure 6B:
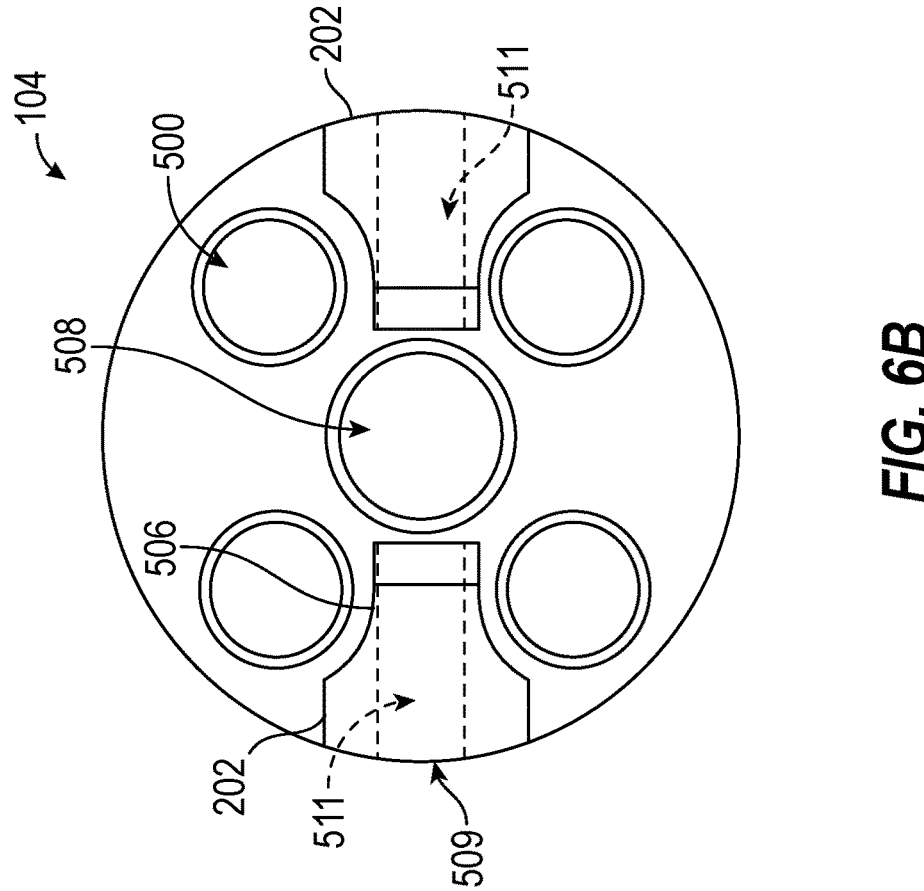
FIGS. 6A-6B are perspective and end views, respectively, of a body bead configured for use with the implantable intramedullary devices of the present technology.
Figure 6A:
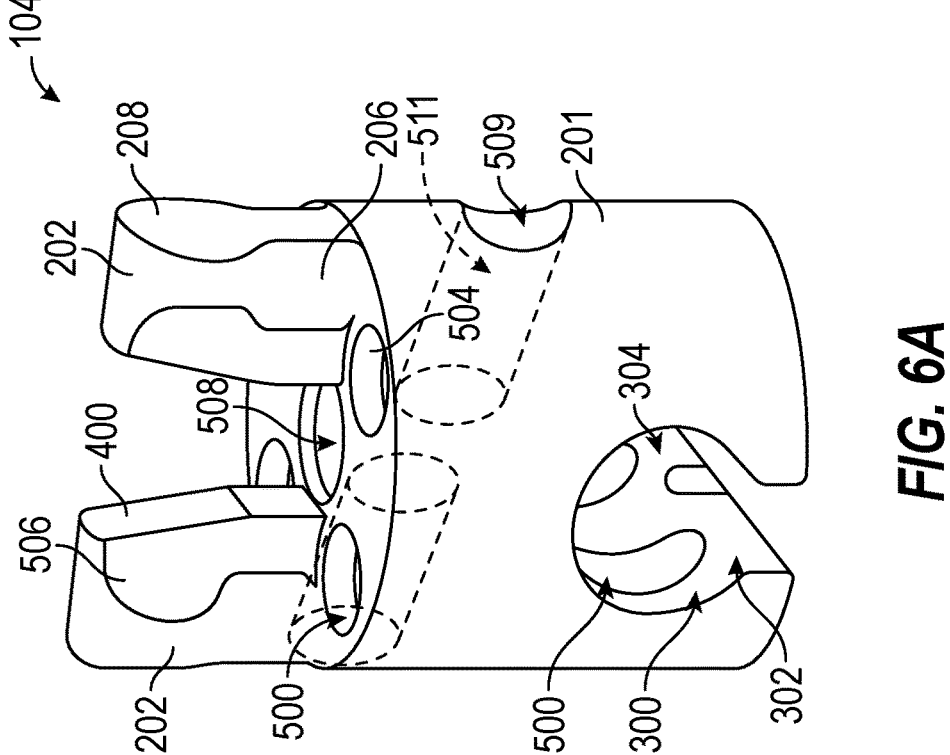

FIGS. 6A and 6B illustrate another example of a body bead 104 for use with the device 100. As shown, in some embodiments of the device 100, one, some, or all of the body beads 104 can include at least one exit port 509 in a sidewall thereof which communicates via a transverse channel 511 with central through hole 508. In some embodiments, multiple exit ports 509 are disposed at spaced apart locations around the circumference of bead 104, for example 180 degrees apart as shown in FIGS. 5A and 5B. Other numbers of channels and ports and spacings are possible. Channel locations can be selected such that transverse channels 511 do not intersect with the through holes 500. However, in some embodiments the transverse channels may communicate with the through holes 500 to allow liquid material such as bone cement to be delivered into the through holes 500, thereby assisting in locking the cables in position when the device is in its desired implanted shape.

Figures 7A, 7B:
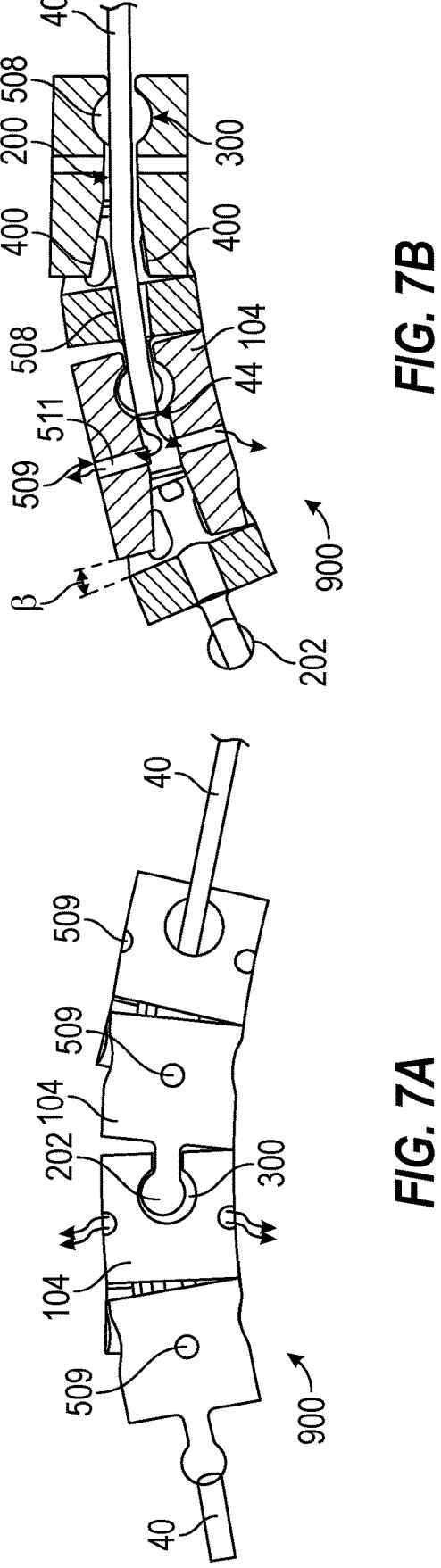
FIGS. 7A-7B are side elevation and side cross-section, respectively, of a portion of an implantable intramedullary device of the present technology incorporating the body bead of FIGS. 6A-6B.

FIGS. 7A and 7B illustrate a segment 900 of the device 100 having at least a few beads having exit ports. In FIGS. 7A and 7B, the device 100 is locked in a curved shape and positioned within an intramedullary channel of a bone (not shown). A flexible fluid delivery catheter (e.g., catheter 40, etc.) is shown inserted into the delivery channel 200. The catheter 40 may be inserted and advanced to a desired axial position within the delivery channel 200, such that the delivery port 44 is disposed within a selected bead 104, or near a selected exit port 509. Liquid material such as bone cement or biologic or pharmacologic materials may then be delivered via the catheter 40 into the delivery channel 200, from which the liquid material flows through the transverse channels 511 and exit ports 509 into the intramedullary channel. In some embodiments, catheter 40 is configured to fit snugly but slidably within through holes 508 so that liquid material is inhibited from flowing proximally from the delivery port 44. In other embodiments, catheter 40 is of smaller diameter than through hole 508 to allow flow of material both distally and proximally.

In some embodiments, the device 100 may include a tubular sleeve or series of tubular sleeves (not shown) extending between two or more adjacent beads 104 and interconnecting the central through holes 508 therein. The tubular sleeve or sleeves may pass through, or partially through, central through holes 508 and may be fixed to beads 104 therein, so as not to block transverse channels 511 or exit ports 509. Such tubular sleeves may be composed of a flexible polymer to allow relative movement of adjacent beads and will be configured to inhibit fluid leakage through gaps G between adjacent beads. In this way, the liquid material may be directed specifically to the exit ports 509 without flowing through gaps G. In some embodiments, the tubular sleeves may extend between a selected plurality of beads 104 in a more proximal region of the device 100, while no sleeves extend between beads 104 in a distal region of device 100. In other cases, tubular sleeves may extend between all of the adjacent beads 104 on the device 100. In certain embodiments, the catheter 40 may be configured to pass slidably within the tubular sleeves to deliver liquid material to one or more selected exit ports 509. In some embodiments, the delivery channel 200 may be connected directly to a fluid delivery apparatus at the proximal end portion of the device 100 to allow liquid material to be delivered directly through delivery channel 200 and the tubular sleeve(s) to the exit ports 509.

Figure 8:
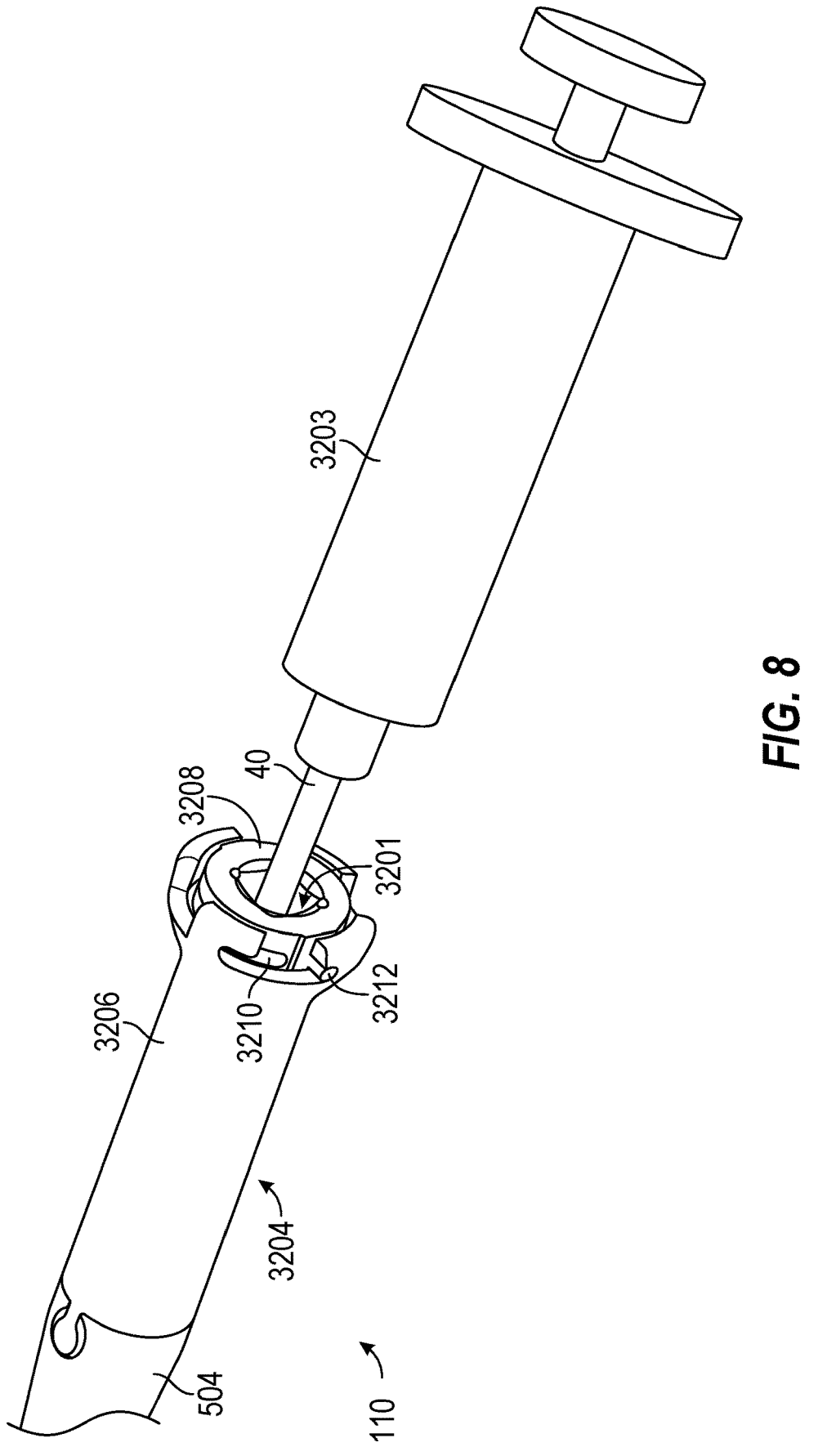
FIG. 8 is a perspective view of a proximal portion of an implantable intramedullary device and fluid delivery apparatus in a further embodiment according to several embodiments of the present technology.

FIG. 8 illustrates an example of several embodiments of a proximal portion 110 of the device 100. The proximal portion 110 includes a housing 3204, a locking mechanism 3208 at its proximal end portion, and a central passage 3201 extending axially through the locking mechanism 3208 to a distal end portion of the housing 3200. At the distal end portion of the housing 110, the central passage 3201 communicates with the delivery channel 200 in the beads 104. The central passage 3201 may be configured for coupling to a fluid delivery system and/or device as described above in connection with FIGS. 1A-2B. For example, the central passage 3201 may include threads, or the housing 3200 may include a luer lock arrangement on its proximal end, to allow a fitting to be coupled to the proximal housing in fluid communication with central passage 3201. The fitting may allow direct connection of a tube or conduit from a fluid delivery system and material source, as described in connection with FIGS. 1A-2B, allowing delivery of liquid material directly into central passage 3201 and thus to delivery channel 200 of the device 100. Alternatively, a delivery catheter 40, as described above, may be slidably inserted into central passage 3201 and advanced into delivery channel 200 of the device. A fluid delivery device, such as a syringe 3203, may be connected to catheter 40 for delivery of liquid material thereto. Additional details regarding the proximal portion 3200 can be found in U.S. patent application Ser. No. 17/286,389, filed Apr. 16, 2021, Publication No. US2021/0386465, which is incorporated herein by reference in its entirety.

Figures 9A, 9B:
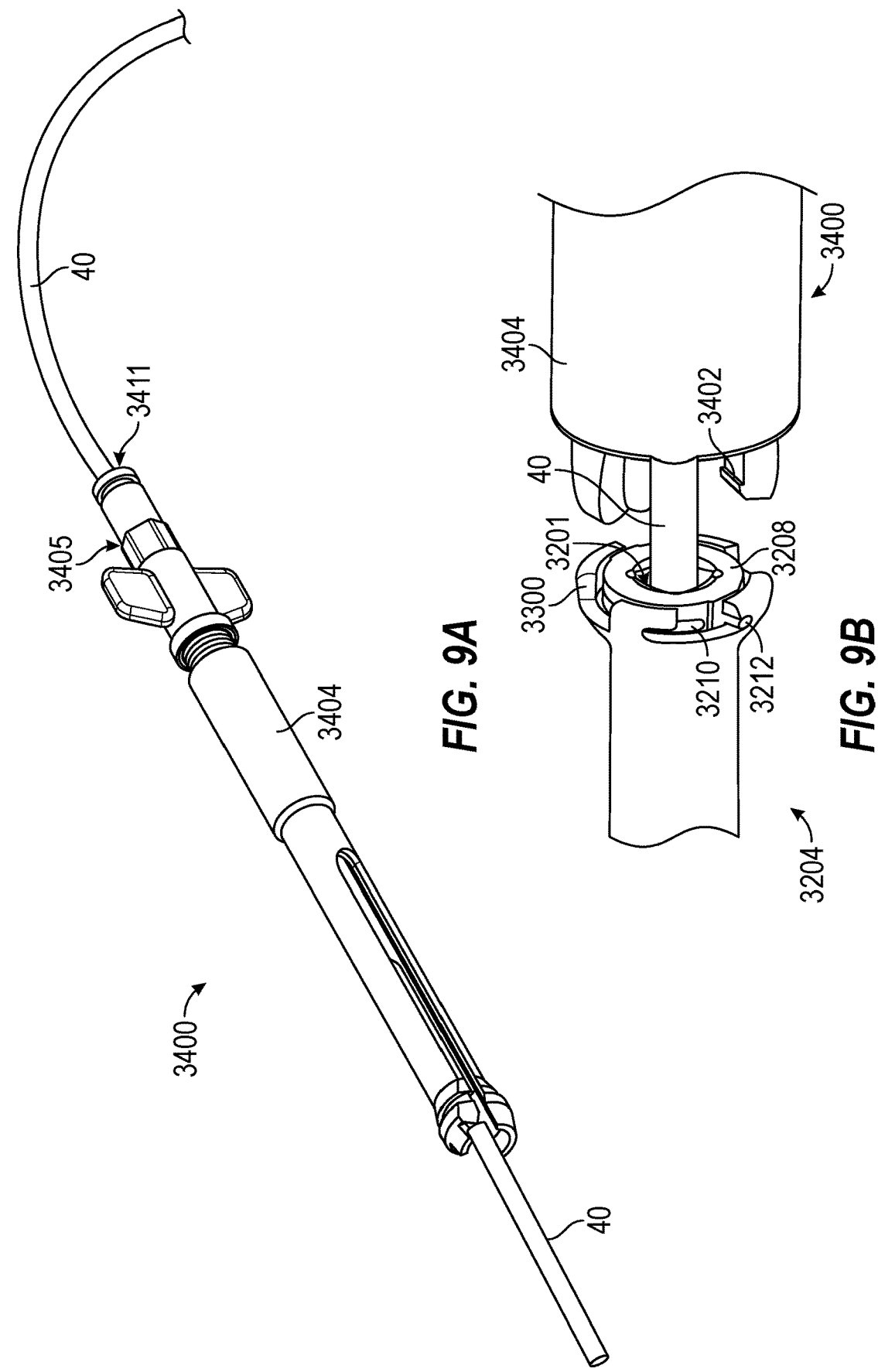
FIG. 9A is a perspective view of an inserter tool for an implantable intramedullary device according to several embodiments of the present technology.
FIG. 9B is an enlarged view of a distal portion of the inserter tool of FIG. 9A in conjunction with a proximal portion of an implantable intramedullary device according to several embodiments of the present technology.

FIGS. 9A and 9B illustrate an inserter tool 3400 for use with the device 100 of the present technology. The inserter tool 3400 is configured to insert, extract, rotate, lock, and unlock the device 100. The inserter tool 3400 attaches to a housing 3204 of proximal portion 3200 and securely holds onto the device and allows the locking mechanism 3208 to be actuated (e.g. rotated) in order to lock the device into a rigid configuration. Tangs 3402 of the tool 3400 are placed into open slots 3300 of the proximal housing 3204. An outer tube 3404 of the tool 3400 is movable distally down the length of the tool to press the tangs 3402 inward toward the locking mechanism 3208 of the device. The ends of the tangs 3402 are captured in a groove 3210 of the proximal lock 3208. When pressed inward enough, the tangs 3402 are locked into the groove 3210 and, therefore, the tool 3400 is securely attached to the device 3200. A lock activator 3405 is rotatable on inserter tool 3400 to actuate the locking mechanism 3208, locking the device in a rigid state.

Inserter tool 3400 may be configured to receive and guide a delivery catheter 40 into the delivery channel 200 of device 100 while the inserter is coupled to the device. Advantageously, this permits the surgeon to insert the device in the intramedullary channel, actuate the locking mechanism, then deliver liquid material such as bone cement through the device, without removal of the inserter tool from the device, and without having to manipulate the catheter through the skin incision and into the proximal end of the device manually. As shown in FIG. 9A, inserter tool 3400 may include a central bore or passage 3411 extending axially through lock activator 3404 and through the entire length of inserter tool 3400. As may be seen in FIG. 9B, the central bore 3411 aligns with central passage 3201 in proximal housing 3204 of the device, allowing catheter 40 to be advanced from central bore 3411 into the central passage 3201, and from there into delivery channel 200 of the device.

In other embodiments, inserter tool 3400 is configured to be coupled to proximal housing 3404 in a manner which creates a fluid tight interconnection between central bore 3411 and central passage 3201. In such embodiments, the proximal end of lock actuator 3405 is configured for fluid connection of central bore 3411 to a fluid delivery apparatus, and may include a luer lock or other suitable fitting. In this way, liquid material may be delivered from the fluid delivery apparatus directly into central bore 3411, from which it passes into delivery channel 200 of the device, without the need for insertion of a separate catheter.

Additional details regarding the inserter tool can be found in U.S. application Ser. No. 17/286,389, filed Apr. 16, 2021, Publication No. US2021/0386465, which is incorporated herein by reference in its entirety.

Figure 10:
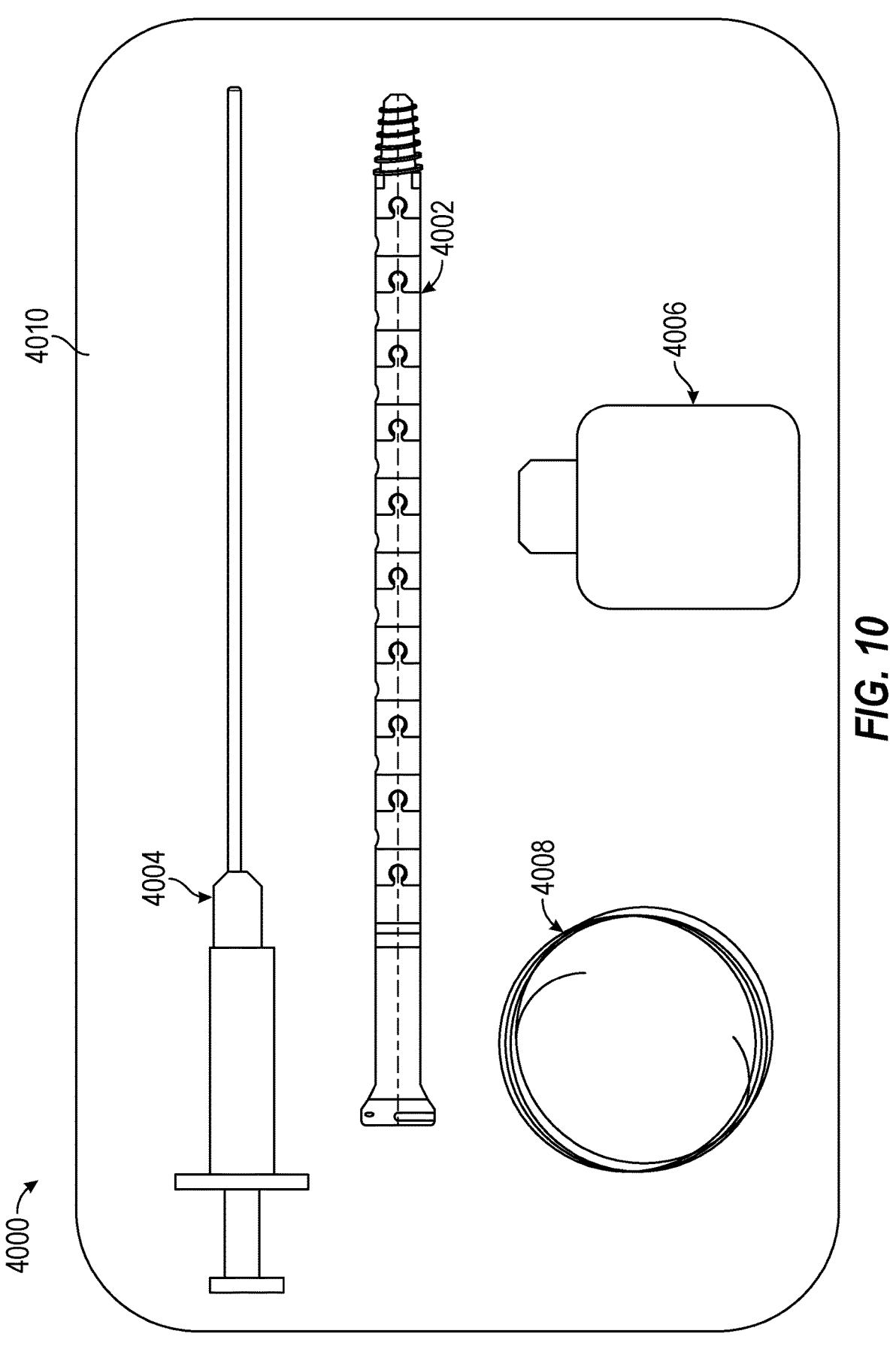
FIG. 10 is a schematic of an intramedullary treatment system according to several embodiments of the present technology.

FIG. 10 illustrates an intramedullary treatment system 4000 according to several embodiments of the present technology. System 4000 includes an implantable intramedullary device 4002, which may comprise any of the intramedullary devices described in this application. System 4000 further includes a fluid delivery apparatus 4004, which may comprise one or more of a syringe, power injector, pump, fluid delivery catheter, or hypotube as described elsewhere herein, and such tubing and fittings as are needed for fluid connection to intramedullary device 4002. A liquid material, or one or more components thereof in liquid or dry form, may be provided in one or more material containers 4006. The liquid material may comprise, as described above, bone cement, a biologic, a pharmacologic solution, or other material useful in conjunction with the implantable intramedullary devices of the invention.

Optionally, the system 4000 may further include a guidewire 4008 for use with flexible embodiments of intramedullary device 4002 for guidance into curved intramedullary channels. Alternatively or additionally, for embodiments in which fluid delivery apparatus comprises a flexible delivery catheter, guidewire 4008 may be provided for use with such a delivery catheter for guidance into an intramedullary channel prior to insertion of the intramedullary device 4002. In some cases, the same guidewire may be used both for guiding the delivery catheter and, following liquid material delivery and removal of the catheter, for guiding the intramedullary device in the intramedullary channel. Further, system 4000 may include an inserter tool (not shown in FIG. 10), as described above in connection with FIGS. 9A-9B, which may, in some embodiments, be a single-use disposable. Optionally, a portion or all of these system components may be packaged together in a sterilized package 4010 in the form of a kit, or may be otherwise supplied to the user together as companion products.

Each of U.S. Pat. No. 9,839,435, issued Dec. 12, 2017, U.S. Pat. No. 9,498,264, issued Nov. 22, 2016, U.S. Pat. No. 10,307,188, issued Jun. 4, 2019, U.S. Pat. No. 10,258,394, issued Apr. 16, 2019, U.S. Pat. No. 10,973,559, issued Apr. 13, 2021, PCT Publication No. WO 2020/077457, filed Oct.

17, 2019, and PCT Publication No. WO 2020/081855, filed Oct. 17, 2019, discloses intramedullary fixation devices for use in treating fractures of the pelvis and is incorporated herein by reference in its entirety. Any of the intramedullary devices disclosed in the foregoing references, as well as other intramedullary devices, can be used in conjunction with the methods, systems, and/or devices disclosed in this application.

The devices and methods disclosed herein can be used, for example, in the treatment of one or more of the following conditions and in the corresponding procedures: (1) fractures of the pelvis; (2) conditions of, and procedures for, sacroiliac joint and pubic symphysis; (3) conditions of, and procedures for, the spine, such as spinal fusion, scoliosis, kyphosis, and kyphoscoliosis; (4) fractures of curved bones including proximal femur, proximal humerus, distal humerus, radius, ulna, mandible (lower jaw), calcaneus (heel bone) and ribs; (5) total hip replacement or other joint replacement; (6) revision surgery for replacement of failed artificial joints (e.g. hip or knee joints); (7) treatment of fractures in curved bones caused by osteoporosis or other disease of the bone; and (8) treatment of bone conditions caused by deformities, cancer or other bone diseases. It will be appreciated that the devices and methods disclosed herein can be used to treat additional conditions.

Potential advantages of the intramedullary implants of the present technology for one or more of the aforementioned devices and procedures versus existing techniques and devices include: (1) Stronger holding forces of the flexible intramedullary device in weakened or missing bone. Examples of this are: fixing high impact fractures with missing bone fragments, fixing low impact fractures in osteoporotic or osteopenic bone, fixing bone weakened by tumors or by cancer treatment, or fixing an artificial joint in the case of bone loss due to revision of an artificial joint such as a hip joint. (2) Bonding the intramedullary device to a prosthetic bone implant. The prosthetic implant may be designed to fill gaps within damaged bone. (3) Ability to deliver bone cement, biologics or other materials at one or more predetermined locations along the axial length of the implant. (4) Ability to convert the intramedullary implant into a rigid state with the use of bone cement, biologics or other materials. For example, the injected agent could be used to lock the curvature of the flexible implant. In some examples of these embodiments, the injected agent could fill in gaps or spaces within the flexible section of the implant. After hardening, injected agent would limit motion of the flexible section and convert the implant from a flexible state to a rigid state.

CONCLUSION

Although many of the embodiments are described above with respect to systems, devices, and methods for fixing bones, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-10.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for treating a fractured bone, the device comprising:
  an elongate body configured for implantation in an intramedullary channel in the bone, the elongate body including:
    a delivery channel extending axially through at least a portion of the elongate body, the delivery channel configured to slidingly receive a tube or catheter coupled to a fluid delivery device,
    an inlet port in communication with the delivery channel and configured for fluid coupling to the fluid delivery device, wherein the inlet port is adapted to receive the tube or catheter therethrough, and
    an exit port in communication with the delivery channel,
  wherein the delivery channel, inlet port, and exit port are configured for delivery of a liquid material from the fluid delivery device into the intramedullary channel,
  wherein the tube or catheter is configured to be advanced a selectable distance in the delivery channel to deliver the liquid material to the exit port.

2. The device of claim 1, wherein the elongate body has a flexible state and a rigid state, and wherein, in the flexible state, the elongate body is configured to follow a curved intramedullary channel during insertion of the device into the curved intramedullary channel.

3. The device of claim 2, wherein the elongate body is lockable in the rigid state after insertion.

4. The device of claim 3, wherein the elongate body is lockable in a curved shape in the rigid state.

5. The device of claim 2, further comprising a locking mechanism for locking the elongate body in the rigid state.

6. The device of claim 5, wherein a proximal portion of the elongate body is configured to be coupled to an inserter device for inserting the intramedullary device in the bone.

7. The device of claim 6, wherein the locking mechanism is configured to be coupled to an actuator in the inserter device, and wherein actuation of the actuator locks the elongate body in the rigid state.

8. The device of claim 1, wherein the inlet port is disposed at a proximal portion of the elongate body.

9. The device of claim 1, further comprising a fitting in fluid communication with the inlet port and configured for coupling to a fluid delivery apparatus.

10. The device of claim 1, wherein a proximal portion of the elongate body is configured to be coupled to an inserter device for inserting the device in the bone, and the inlet port is configured for fluid coupling to an introduction channel in the inserter device.

11. The device of claim 1, wherein the elongate body includes a plurality of exit ports, and the tube or catheter can be advanced a selectable distance in the delivery channel to deliver the liquid material to a selected one or more exit ports.

12. The device of claim 1, wherein the elongate body includes one or more radiopaque fiducials to allow visualization of a location of the tube or catheter relative to the elongate body.

13. The device of claim 12, wherein the elongate body is at least partially radiopaque, and the tube or catheter is at least partially radiopaque or includes one or more radiopaque fiducials to allow visualization of a location of the tube or catheter relative to the elongate body.

14. The device of claim 13, further comprising a seal configured to provide a fluid seal around the tube or catheter when inserted into the delivery channel.

15. The device of claim 1, wherein the inlet port, delivery channel, and exit ports are configured for delivery of a material having a viscosity of about 10-100 cP under a delivery pressure of no more than about 300 psi.

16. The device of claim 2, wherein the elongate body comprises a plurality of beads movably coupled to each other.

17. The device of claim 16, wherein each bead of the beads is pivotable about a transverse axis relative to an adjacent bead.

18. The device of claim 16, wherein the delivery channel extends axially through at least some of the beads.

19. The device of claim 18, wherein the exit ports comprise openings between adjacent beads.

20. The device of claim 18, wherein the exit ports comprise openings in a sidewall of at least a portion of the beads.

21. The device of claim 18, wherein the delivery channel is fluidly sealed between at least a portion of adjacent beads.

22. The device of claim 21, wherein the delivery channel comprises a continuous flexible tube extending through a plurality of the beads.

* * * * *